United States Patent
Bigg et al.

(10) Patent No.: US 7,402,602 B2
(45) Date of Patent: Jul. 22, 2008

(54) IMIDAZOLE DERIVATIVES MODULATING THE SODIUM CHANNELS

(75) Inventors: Dennis Bigg, Gif-sur-Yvette (FR); Jacques Pommier, Paris (FR); Anne-Marie Liberatore, Auffargis (FR)

(73) Assignee: Societe de Conseils de Recherches Et d'Applications Scientifiques (S.C.R.A.S), Paris (FR)

( * ) Notice: Subject to any disclaimer, the term of this patent is extended or adjusted under 35 U.S.C. 154(b) by 0 days.

(21) Appl. No.: 11/281,864

(22) Filed: Nov. 17, 2005

(65) Prior Publication Data

US 2006/0069146 A1    Mar. 30, 2006

Related U.S. Application Data

(62) Division of application No. 10/480,977, filed as application No. PCT/FR02/02039 on Jun. 14, 2002.

(30) Foreign Application Priority Data

Jun. 15, 2001    (FR) .................................. 01 07820

(51) Int. Cl.
*A61K 31/4164* (2006.01)
(52) U.S. Cl. .................................... 514/396; 548/343.5
(58) Field of Classification Search .................. 514/396
See application file for complete search history.

(56) References Cited

FOREIGN PATENT DOCUMENTS

| GB | 1046248 | * | 10/1966 |
| WO | WO-0071120 A1 | * | 11/2000 |

OTHER PUBLICATIONS

Gregory Y. H. Lip et al., The Pharmaceutical Journal, vol. 264, No. 7093, pp. 622-626, Apr. 22, 2000.*

* cited by examiner

*Primary Examiner*—Laura L Stockton
(74) *Attorney, Agent, or Firm*—Charles A. Muserlian

(57) ABSTRACT

A method of treating cardiac rhythm disorders linked with neurodegenerating depression, bipolar disorders and irritable bowel disorders in warm-blooded animals in need thereof by administering a compound of the formula

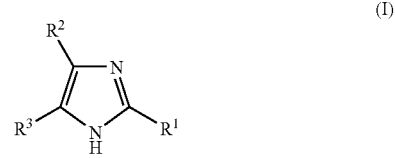

(I)

wherein the substituents are defined as in the specification.

3 Claims, No Drawings

IMIDAZOLE DERIVATIVES MODULATING THE SODIUM CHANNELS

PRIOR APPLICATION

This application is a division of U.S. patent application Ser. No. 10/480,977 filed Dec. 15, 2003 which is a 371 of PCT/FR02/02039 filed Jun. 14, 2002.

The present invention relates to new imidazole derivatives modulating the sodium channels, their preparation and their therapeutic uses.

Sodium channel modulating compounds are very useful for therapeutic uses such as:

the treatment or prevention of pain, and in particular:
neuropathic pain such as trigeminal neuralgia, pain associated with viral or retroviral diseases (for example pain linked to herpes such as post-herpetic pain, pain associated with Acquired Immune Deficiency Syndrome (AIDS) or pain linked to shingles), diabetic neuropathies, glosso-pharyngeal neuralgia, secondary radiculopathies and neuropathies associated with metastatic infiltrations, adiposis dolorosa and pain associated with burns,
migraine,
post-operative pain,
central pain as a result of vascular cerebral accidents, thalamic lesions and multiple sclerosis,
chronic pain, and
pain linked with a cancer;
the treatment of epilepsy;
the treatment of cardiac rhythm disorders;
the treatment of disorders linked with neurodegeneration, and in particular:
vascular cerebral accidents,
cerebral trauma, and
neurodegenerative diseases such as Alzheimer's disease, Parkinson's disease and amyotrophic lateral sclerosis;
the treatment of depression and bipolar disorders;
the treatment of irritable bowel syndrome;
the treatment of diabetic retinopathies.

The compounds corresponding to general formula (I) as defined below are sodium channel modulators and are therefore capable of being used for the treatment of the diseases/disorders mentioned previously.

Patent Application PCT WO 95/00493 describes synthesis intermediates of general formula (A1)

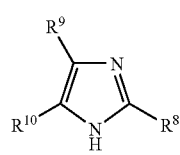

(A1)

in which:
$R^8$ represents in particular an alkyl radical containing from 1 to 6 carbon atoms or an optionally substituted phenylalkyl radical;
and $R^9$ and $R^{10}$ represent in particular independently a hydrogen atom, an alkyl radical containing from 1 to 6 carbon atoms or a phenyl radical optionally substituted by one or more radicals chosen in particular from a halogen atom and a hydroxy, alkyl or alkoxy radical.

However, no pharmacological property is described for these compounds.

U.S. Pat. No. 5,840,721 describes agents useful for restoring the sensitivity of cancerous cells resistant to treatment by chemotherapy agents, said agents corresponding to general formula (A2)

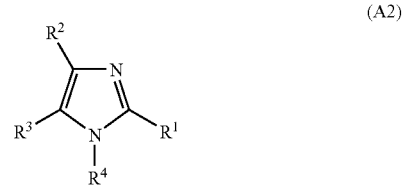

(A2)

in which:
$R^1$ represents in particular an optionally substituted aralkyl radical;
$R^2$ and $R^3$ represent in particular independently a hydrogen atom, an alkyl radical containing from 1 to 6 carbon atoms or a phenyl radical optionally substituted by one or more radicals chosen in particular from a halogen atom and an alkyl or alkoxy radical;
and $R^4$ represents in particular a hydrogen atom.

Patent Application PCT WO 00/57877 describes sodium channel blocking agents, and in particular those of general formula (A3)

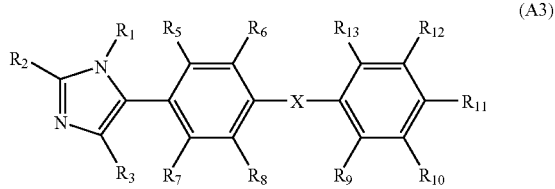

(A3)

in which:
$R_1$ represents in particular a hydrogen atom;
$R_2$ and $R_3$ represent in particular independently a hydrogen atom or an alkyl radical with 1 to 10 carbon atoms, a cycloalkyl radical or an aryl radical,
X represents O, S or an $NR_{15}$ radical in which $R_{15}$ represents a hydrogen atom, an alkyl or cycloalkyl radical,
and $R_5$, $R_6$, $R_7$, $R_8$, $R_9$, $R_{10}$, $R_{11}$, $R_{12}$ and $R_{13}$ represent (in particular) independently a hydrogen atom, a halogen atom and an alkyl, hydroxy or alkoxy radical.

Patent Application PCT WO 01/26656 describes sodium channel modulating agents, and in particular those of general formula (A4)

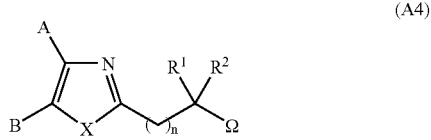

(A4)

in which:
A represents (in particular) an optionally substituted phenyl or biphenyl radical;

B represents (in particular) a hydrogen atom or an alkyl radical;

X represents (in particular) $NR^{38}$, $R^{38}$ representing in particular a hydrogen atom or an alkyl radical;

n is an integer from 0 to 6;

Ω represents one of the $NR^{46}R^{47}$ or $OR^{48}$ radicals in which $R^{46}$ and $R^{47}$ represent (in particular), independently, a hydrogen atom or an alkyl, cycloalkyl or cycloalkylalkyl radical and $R^{48}$ represents a hydrogen atom or an alkyl radical.

However, as in a number of prior documents presented in PCT Patent Application WO 00/57877, the phenoxyphenyl (X represents O) or phenylthiophenyl (X represents S) or anilinophenyl (X represents $NR_{15}$) unit appears to be one of the essential elements for obtaining a sodium channel modulation activity.

Moreover, PCT Patent Application WO 00/71120 describes agents with antibacterial activity which correspond in particular to general formula (A5)

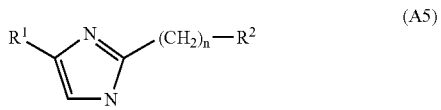

in which:

$R^1$ represents a $C_{1-4}$ alkyl, Ar, 2-thienyl or 3-thienyl radical;

$R^2$ represents a $C_{1-4}$ alkyl, Ar radical;

n is an integer from 0 to 3; and

Ar represents phenyl or naphthyl optionally substituted from 1 to 3 times by substituents such as $C_{1-4}$ alkyl, $C_{1-4}$ alkoxy, $CF_3$, F, Cl, Br, I, phenyl or methylenedioxy, said substituents being able to be obtained by chemical synthesis and being stable.

PCT Patent Application WO 01/44201 describes antagonists of the Y5 receptor of the Y neuropeptide which correspond in particular to general formula (A6)

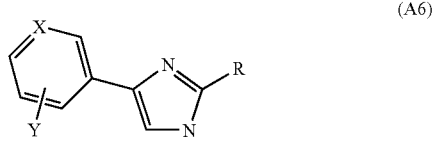

in which:

R represents (in particular) a $C_1$-$C_6$ alkyl, $C_3$-$C_7$ cycloalkyl, heterocycloalkyl, heterocycloalkyl($C_1$-$C_6$)alkyl or heteroaryl($C_1$-$C_6$)alkyl radical or also the

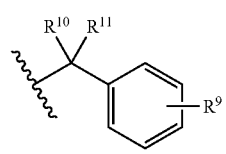

radical, $R^9$ representing from one to three substituents chosen independently from a hydrogen atom, a halogen atom and a $C_1$-$C_6$ alkyl or $C_1$-$C_6$ alkoxy radical, and $R^{10}$ and $R^{11}$ being (in particular) chosen independently from a hydrogen atom and a $C_1$-$C_6$ alkyl radical;

X represents =CH— or =N—; and

Y represents from one to three substituents chosen independently from a hydrogen atom, a halogen atom or a trihaloalkyl, $C_1$-$C_6$ alkyl, $C_1$-$C_6$ alkenyl, $C_3$-$C_7$ cycloalkyl, $C_1$-$C_6$ alkyl radical substituted by $C_3$-$C_7$ cycloalkyl, —OH, —O($C_1$-$C_6$)alkyl, —SH, —S($C_1$-$C_6$)alkyl, or —CN.

Finally, an article by Suenaga et al. (*Tetrahedron Letters* (2001), 42, 7079-81) describes catharsitoxins D and E, i.e. respectively 2-(2-methylpropyl)-5-phenylimidazole and 2-(1-methylpropyl)-5-phenylimidazole. The biological properties of these toxins should however also be studied.

According to the invention, the compounds of general formula (1)

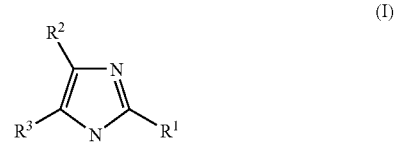

in which $R^1$ represents a linear or branched alkyl radical containing from 3 to 16 carbon atoms (and preferably from 4 to 16 carbon atoms and more preferentially still from 6 to 12 carbon atoms) or cycloalkylalkyl, or also $R^1$ represents an aralkyl radical optionally substituted from 1 to 3 times on the aryl group by substituents chosen independently from a halogen atom and an alkyl or alkoxy radical;

$R^2$ represents a phenyl radical optionally substituted from 1 to 3 times by substituents chosen independently from a halogen atom and an alkyl or alkoxy radical, or also $R^2$ represents a biphenyl radical optionally substituted from 1 to 4 times by one or more substituents chosen independently from a halogen atom and an alkyl or alkoxy radical;

$R^3$ represents a hydrogen atom or an alkyl radical;

and the pharmaceutically acceptable salts of the latter;

can be used for preparing a medicament intended to modulate the sodium channels.

By alkyl, unless otherwise specified, is meant a linear or branched alkyl radical containing from 1 to 12 carbon atoms, and preferably from 1 to 6 carbon atoms. By cycloalkyl, unless otherwise specified, is meant a monocyclic carbon system containing 3 to 7 carbon atoms. By aryl, unless otherwise specified, is meant a carbocyclic aryl radical. By carbocyclic aryl, is meant a carbocyclic system comprising at least one aromatic ring (and, in particular, the phenyl radical, which can be abbreviated to Ph, or the naphthyl radical).

By alkoxy, aralkyl and cycloalkylalkyl radicals, is meant respectively the alkoxy, aralkyl and cycloalkylalkyl radicals, the alkyl radical of which has the meaning indicated previously. By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. Finally, by halogen atom, is meant the fluorine, chlorine, bromine or iodine atoms.

By pharmaceutically acceptable salt, is meant in particular addition salts of inorganic acids such as hydrochloride, hydrobromide, hydroiodide, sulphate, phosphate, diphosphate and nitrate or organic acids such as acetate, maleate, fumarate, tartrate, succinate, citrate, lactate, methanesulphonate, p-toluenesulphonate, pamoate and stearate. Also within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

Preferably, the compounds of general formula (I) are such that they will possess at least one of the following characteristics:

$R^1$ representing a linear or branched alkyl radical containing 3 to 16 carbon atoms or cycloalkylalkyl, or also $R^1$ representing an aralkyl radical optionally substituted from 1 to 3 times on the aryl group by substituents chosen independently from alkyl radicals;

$R^2$ representing a phenyl radical optionally substituted from 1 to 3 times by substituents chosen independently from a halogen atom and an alkyl radical, or also $R^2$ representing a biphenyl radical optionally substituted from 1 to 4 times by one or more substituents chosen independently from a halogen atom and an alkyl radical;

$R^3$ representing a hydrogen atom.

More preferentially, the compounds of general formula (I) are such that they will possess at least one of the following characteristics:

$R^1$ representing a linear or branched alkyl radical containing from 4 to 16 carbon atoms or a cycloalkylalkyl radical in which the alkyl radical contains from 1 to 4 carbon atoms, or also $R^1$ representing an aralkyl radical in which the alkyl radical contains from 1 to 4 carbon atoms, said aralkyl radical optionally substituted from 1 to 3 times on the aryl group by substituents chosen independently from alkyl radicals;

$R^2$ representing a phenyl radical optionally substituted from 1 to 3 times by substituents chosen independently from a halogen atom and an alkyl radical, or also $R^2$ representing a biphenyl radical optionally substituted from 1 to 4 times by one or more halogen atoms;

$R^3$ representing a hydrogen atom.

Still more preferentially, the compounds of general formula (I) are such that they will possess at least one of the following characteristics:

$R^1$ representing a linear or branched alkyl radical containing from 6 to 16 carbon atoms or a cycloalkylalkyl radical in which the alkyl radical contains from 1 to 4 carbon atoms, or also $R^1$ representing an aralkyl radical in which the alkyl radical contains from 1 to 4 carbon atoms, said aralkyl radical optionally substituted from 1 to 3 times on the aryl group by substituents chosen independently from alkyl radicals;

$R^2$ representing a phenyl radical optionally substituted from 1 to 3 times by substituents chosen independently from a halogen atom and an alkyl radical, or also $R^2$ representing a biphenyl radical optionally substituted by a halogen atom;

$R^3$ representing a hydrogen atom.

In a particularly preferred fashion, the compounds of general formula (I) will be such that $R^1$ represents a branched alkyl radical containing from 6 to 16 carbon atoms, more particularly from 7 to 16 carbon atoms and still more particularly from 8 to 16 carbon atoms (and in particular from 8 to 12 carbon atoms). In particular, the case will be preferred where $R^1$ will represent a —$CHR^4R^5$ radical in which $R^4$ will represent a —$(CH_2)_p$—$CH_3$ radical and $R^5$ will represent a —$(CH_2)_p$—$CH_3$ radical, p and q being integers such that their sum p+q is greater than or equal to 7 and less than or equal to 16, and preferably greater than or equal to 8 or 10 and less than or equal to 12 or 16.

Also in a particularly preferred fashion, the compounds of general formula (I) are such that $R^1$ represents a cycloalkylalkyl radical, in which the alkyl radical preferably contains from 1 to 4 carbon atoms (the cycloalkyl radical being preferably a cyclohexyl radical).

Still in a particularly preferred fashion, the compounds of general formula (I) are such that $R^2$ represents a biphenyl radical optionally substituted by a halogen atom or an alkyl radical (and preferably a biphenyl radical substituted by a halogen atom or an alkyl radical, in particular a biphenyl radical substituted by a halogen atom).

According to the invention, the compounds of general formula (I) can in particular be used for preparing a medicament intended for the treatment or prevention of pain, the treatment or prevention of epilepsy, the treatment of cardiac rhythm disorders, the treatment of disorders linked with neurodegeneration, the treatment of depression and bipolar disorders, the treatment of irritable bowel syndrome or the treatment of diabetic retinopathies. Preferably, the medicament prepared is intended for the treatment or prevention of pain or epilepsy (and more preferentially the treatment or prevention of pain).

In particular, the invention relates to the above-mentioned uses using the following compounds of general formula (I) (described in the examples):

4-(1,1'-biphenyl-4-yl)-2-(4-isobutylbenzyl)- 1H-imidazole;
2-hexyl-4-(4-isobutylphenyl)-1H-imidazole;
4-phenyl-2-(3-phenylpropyl)-1H-imidazole;
2-(1-pentylhexyl)-4-phenyl-1H-imidazole;
4-(4-fluorophenyl)-2-(1-pentylhexyl)-1H-imidazole;
2-(cyclohexylmethyl)-4-(4-fluorophenyl)-1H-imidazole;
4-(1,1'-biphenyl-4-yl)-2-(1-pentylhexyl)-1H-imidazole;
4-(4-tert-butylphenyl)-2-(1-propylbutyl)-1H-imidazole;
4-(4-fluorophenyl)-2-(1-propylbutyl)-1H-imidazole;
4-(4'-bromo-1,1'-biphenyl-4-yl)-2-(1-propylbutyl)-1H-imidazole;
4-(1,1'-biphenyl-4-yl)-2-(2-cyclohexylethyl)-1H-imidazole;
4-(1,1'-biphenyl-4-yl)-2-hexyl-1H-imidazole;
4-(1,1'-biphenyl-4-yl)-2-[1-(4-isobutylphenyl)ethyl]-1H-imidazole;
4-(4-fluorophenyl)-2-[1-(4-isobutylphenyl)ethyl]-1H-imidazole;
4-(1,1'-biphenyl-4-yl)-2-(1-phenylethyl)-1H-imidazole;
4-(1,1'-biphenyl-4-yl)-2-(1-propylbutyl)-1H-imidazole;
4-(1,1'-biphenyl-4-yl)-2-(cyclohexylmethyl)-1H-imidazole;
4-(1,1'-biphenyl-4-yl)-2-(3-cyclohexylpropyl)-1H-imidazole;

as well as the pharmaceutically acceptable salts of the latter.

For this use, the following compounds are preferred:
4-(1,1'-biphenyl-4-yl)-2-(4-isobutylbenzyl)-1H-imidazole;
2-hexyl4-(4-isobutylphenyl)-1H-imidazole;
2-(1-pentylhexyl)4-phenyl-1H-imidazole;
4-(4-fluorophenyl)-2-(1-pentylhexyl)-1H-imidazole;
4-(1,1'-biphenyl-4-yl)-2-(1-pentylhexyl)-1H-imidazole;
4-(4-tert-butylphenyl)-2-(1-propylbutyl)-1H-imidazole;
4-(1,1'-biphenyl-4-yl)-2-(2-cyclohexylethyl)-1H-imidazole;
4-(1,1'-biphenyl-4-yl)-2-hexyl- 1H-imidazole;
4-(1,1'-biphenyl-4-yl)-2-[1-(4-isobutylphenyl)ethyl]-1H-imidazole;
4-(1,1'-biphenyl-4-yl)-2-(1-propylbutyl)-1H-imidazole;
4-(1,1'-biphenyl-4-yl)-2-(cyclohexylmethyl)-1H-imidazole;
4-(1,1'-biphenyl-4-yl)-2-(3-cyclohexylpropyl)-1H-imidazole;

as well as the pharmaceutically acceptable salts of the latter.

The invention also relates to the compounds of general formula (II), as medicaments

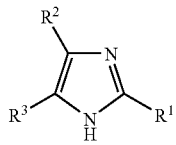

in which
R¹ represents a linear or branched alkyl radical containing from 3 to 16 carbon atoms (and preferably from 4 to 16 carbon atoms and more preferentially still from 6 to 12 carbon atoms) or cycloalkylalkyl,
or also R¹ represents an aralkyl radical optionally substituted from 1 to 3 times on the aryl group by substituents chosen independently from a halogen atom and an alkyl or alkoxy radical;
R² represents a phenyl radical optionally substituted from 1 to 3 times by substituents chosen independently from a halogen atom and an alkyl or alkoxy radical,
or also R² represents a biphenyl radical optionally substituted from 1 to 4 times by one or more substituents chosen independently from a halogen atom and an alkyl or alkoxy radical;
R³ represents a hydrogen atom or an alkyl radical;

is it being understood however that:
when R² represents a phenyl radical optionally substituted from 1 to 3 times by substituents chosen independently from a halogen atom and an alkyl or alkoxy radical, then R¹ represents neither a linear or branched alkyl radical containing from 1 to 6 carbon atoms nor a

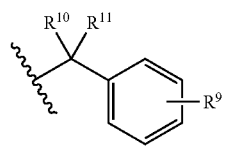

radical,
in which R⁹ represents from one to three substituents chosen independently from a hydrogen atom, a halogen atom and a linear or branched alkyl or alkoxy radical containing from 1 to 6 carbon atoms, and R¹⁰ and R¹¹ being (in particular) chosen independently from a hydrogen atom and a linear or branched alkyl radical containing from 1 to 6 carbon atoms;
when R² represents a non-substituted biphenyl radical or when R² represents a phenyl radical optionally substituted from 1 to 3 times by substituents chosen independently from a halogen atom and one of the linear or branched alkyl or alkoxy radicals containing from 1 to 4 carbon atoms, then R¹ represents neither a —(CH₂)ₙ-Z radical in which n is an integer from 0 to 3 and Z represents a linear or branched alkyl radical containing from 1 to 4 carbon atoms or a phenyl or naphthyl radical optionally substituted by 1 to 3 substituents chosen from the group constituted by a halogen atom and the linear or branched alkyl or alkoxy radicals containing from 1 to 4 carbon atoms;

as well as the pharmaceutically acceptable salts of the latter.

In particular, the invention relates to the following compounds of general formula (II), as medicaments:
2-(1-pentylhexyl)4-phenyl-1H-imidazole;
4-(4-fluorophenyl)-2-(1-pentylhexyl)-1H-imidazole;
2-(cyclohexylmethyl)-4-(4-fluorophenyl)-1H-imidazole;
4-(1,1'-biphenyl-4-yl)-2-(1-pentylhexyl)-1H-imidazole;
4-(4-tert-butylphenyl)-2-(1-propylbutyl)-1H-imidazole;
4-(4-fluorophenyl)-2-(1-propylbutyl)-1H-imidazole;
4-(4'-bromo-1,1'-biphenyl-4-yl)-2-(1-propylbutyl)-1H-imidazole;
4-(1,1'-biphenyl-4-yl)-2-(2-cyclohexylethyl)-1H-imidazole;
4-(1,1'-biphenyl-4-yl)-2-[1-(4-isobutylphenyl)ethyl]-1H-imidazole;
4-(1,1'-biphenyl-4-yl)-2-(1-phenylethyl)-1H-imidazole;
4-(1,1'-biphenyl-4-yl)-2-(1-propylbutyl)-1H-imidazole;
4-(1,1'-biphenyl-4-yl)-2-(cyclohexylmethyl)-1H-imidazole;
4-(1,1'-biphenyl-4-yl)-2-(3-cyclohexylpropyl)-1H-imidazole;

or their pharmaceutically acceptable salts.
The preferences expressed for the compounds of general formula (I) apply moreover mutatis mutandis to the compounds of general formula (II).
The invention also relates, as medicaments, to the compounds of general formula (I) or their pharmaceutically acceptable salts chosen from the following compounds:
4-(1,1'-biphenyl-4-yl)-2-(4-isobutylbenzyl)-1H-imidazole;
2-hexyl-4-(4-isobutylphenyl)-1H-imidazole;
4-phenyl-2-(3-phenylpropyl-1H-imidazole;
4-(1,1'-biphenyl-4-yl)-2-hexyl-1H-imidazole;
4-(4-fluorophenyl)-2-[1-(4-isobutylphenyl)ethyl]-1H-imidazole;

and their pharmaceutically acceptable salts.
The invention moreover also relates to the compounds of general formula (III)

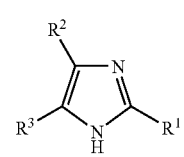

in which
R¹ represents a linear or branched alkyl radical containing from 3 to 16 carbon atoms (and preferably from 4 to 16 carbon atoms and more preferentially still from 6 to 12 carbon atoms) or cycloalkylalkyl,
or also R¹ represents an aralkyl radical optionally substituted from 1 to 3 times on the aryl group by substituents chosen independently from a halogen atom and an alkyl or alkoxy radical;
R² represents a phenyl radical optionally substituted from 1 to 3 times by substituents chosen independently from a halogen atom and an alkyl or alkoxy radical,
or also R² represents a biphenyl radical optionally substituted from 1 to 4 times by one or more substituents chosen independently from a halogen atom and an alkyl or alkoxy radical;
R³ represents a hydrogen atom or an alkyl radical;

it being understood however that:
when R² represents a non-substituted biphenyl radical or when R² represents a phenyl radical optionally substidently from a halogen atom and one of the linear or branched alkyl or alkoxy radicals containing from 1 to 4 carbon atoms, then $R^1$ represents neither a —(CH2)n-Z radical in which n is an integer from 0 to 3 and Z represents a linear or branched alkyl radical containing from 1 to 4 carbon atoms or a phenyl or naphthyl radical optionally substituted by 1 to 3 substituents chosen from the group constituted by a halogen atom and the linear or branched alkyl or alkoxy radicals containing from 1 to 4 carbon atoms; and when $R^2$ represents a phenyl radical optionally substituted from 1 to 3 times by substituents chosen independently from a halogen atom and an alkyl or alkoxy radical, then $R^1$ represents neither a linear or branched alkyl radical containing from 1 to 6 carbon atoms nor a

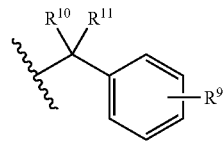

radical, in which $R^9$ represents from one to three substituents chosen independently from a hydrogen atom, a halogen atom and a linear or branched alkyl or alkoxy radical containing from 1 to 6 carbon atoms, and $R^{10}$ and $R^{11}$ being (in particular) chosen independently from a hydrogen atom and a linear or branched alkyl radical containing from 1 to 6 carbon atoms;

as well as the salts of the latter.

In particular, the invention relates, as new industrial products, to the following compounds of general formula (III):
2-(1-pentylhexyl)-4-phenyl-1H-imidazole;
4-(4-fluorophenyl)-2-(1-pentylhexyl)-1H-imidazole;
2-(cyclohexylmethyl)-4-(4-fluorophenyl)-1H-imidazole;
4-(1,1'-biphenyl-4-yl)-2-(1-pentylhexyl)-1H-imidazole;
4-(4-tert-butylphenyl)-2-(1-propylbutyl)-1H-imidazole;
4-(4-fluorophenyl)-2-(1-propylbutyl)-1H-imidazole;
4-(4'-bromo-1,1'-biphenyl-4-yl)-2-(1-propylbutyl)-1H-imidazole;
4-(1,1'-biphenyl-4-yl)-2-(2-cyclohexylethyl)-1H-imidazole;
4-(1,1'-biphenyl-4-yl)-2-[1-(4-isobutylphenyl)ethyl]-1H-imidazole;
4-(1,1'-biphenyl-4-yl)-2-(1-phenylethyl)-1H-imidazole;
4-(1,1'-biphenyl-4-yl)-2-(1-propylbutyl)-1H-imidazole;
4-(1,1'-biphenyl-4-yl)-2-(cyclohexylmethyl)-1H-imidazole;
4-(1,1'-biphenyl-4-yl)-2-(3-cyclohexylpropyl)-1H-imidazole;

or their salts.

The preferences expressed for the compounds of general formula (I) apply moreover *mutatis mutandis* to the compounds of general formula (III), except however for the salts which are not necessarily pharmaceutically acceptable salts.

The invention also relates, as new industrial products, to the compounds of general formula (I) or their salts chosen from:
4-(1,1'-biphenyl-4-yl)-2-(4-isobutylbenzyl)-1H-imidazole;
2-hexyl-4-(4-isobutylphenyl)-1H-imidazole;
4-phenyl-2-(3-phenylpropyl)-1H-imidazole;
4-(1,1'-biphenyl-4-yl)-2-hexyl-1H-imidazole;
4-(4-fluorophenyl)-2-[1-(4-isobutylphenyl)ethyl]-1H-imidazole;

and their salts.

The invention relates moreover to the pharmaceutical compositions comprising, as active ingredient, at least one compound of general formula (II) or (III) as defined previously or a pharmaceutically acceptable salt of such a compound. It also has as a subject the pharmaceutical compositions comprising, as active ingredient, at least one compound described in Examples 1 to 18 (sometimes in the form of salts) or a pharmaceutically acceptable salt of such a compound.

The invention also relates in particular to the pharmaceutical compositions containing, as active ingredient, a compound of general formula (I) or one of its pharmaceutically acceptable salts chosen from:
4-(1,1'-biphenyl-4-yl)-2-(4-isobutylbenzyl)-1H-imidazole;
2-hexyl-4-(4-isobutylphenyl)-1H-imidazole;
4-phenyl-2-(3-phenylpropyl)-1H-imidazole;
4-(1,1'-biphenyl-4-yl)-2-hexyl-1H-imidazole;
4-(4-fluorophenyl)-2-[1-(4-isobutylphenyl)ethyl]-1H-imidazole;

and their pharmaceutically acceptable salts.

The invention also relates to the use of a compound of general formula (II) or (III) as defined previously or a pharmaceutically acceptable salt of such a compound for preparing a medicament intended to modulate the sodium channels.

As regards the medicaments, the pharmaceutical compositions and the above-mentioned uses, the preferences described for the compounds of general formula (I) apply *mutatis mutandis* to the compounds of general formulae (II) and (III).

The pharmaceutical compositions containing a compound of the invention can be in solid form, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or the glycols, as well as their mixtures, in varying proportions, in water.

The administration of a medicament according to the invention can be carried out by topical, oral, parenteral route, by injection intramuscular, etc.

The dose of a product according to the present invention, to be provided for the treatment of the above-mentioned diseases or disorders, varies according to the administration method, the age and body weight of the subject to be treated as well as the state of the latter, and will be finally decided by the attending doctor or vet. Such a quantity determined by the attending doctor or vet is here called "therapeutically effective quantity".

As an indication, the administration dose envisaged for medicaments according to the invention is comprised between 0.1 mg and 10 g depending on the type of active compound used.

According to the invention, the compounds of general formula (I) can be prepared by the processes described hereafter.

PREPARATION OF THE COMPOUNDS OF THE INVENTION

The compounds of general formula (I) can be prepared according to procedures analogous to those described in Application WO 01/26656 and/or according to the procedures explained hereafter. All the compounds of general formula (II) or (III) can of course be prepared in the same fashion as the compounds of general formula (I).

According to the invention, the compounds of general formula (I) can be obtained by a synthesis route summarized in Diagram 1 hereafter.

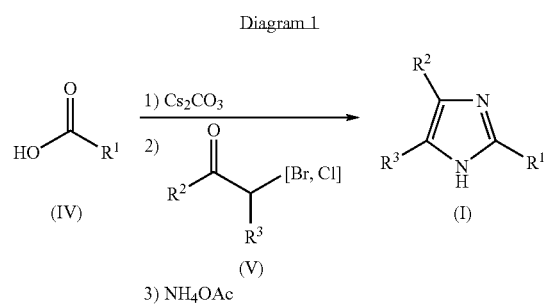

According to this preparation method, the acids of general formula (IV) can be cyclized in the form of imidazole derivatives of general formula (I), Diagram 1, by adding lo cesium carbonate followed by condensation with an α-halogenoketone of general formula (V) followed by the addition of a large excess of ammonium acetate (for example 15 or 20 equivalents per equivalent of acid of general formula (IV)). This reaction is preferably carried out in a mixture of xylenes and while heating (it is also possible, if appropriate, to simultaneously eliminate the water formed during the reaction).

Preparation of Certain Acids of General Formula (IV)

The acids of general formula (IV)$_1$

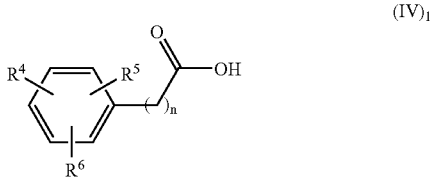

in which $R^4$, $R^5$ and $R^6$ represent independently hydrogen atoms or an alkyl radical and n preferably represents an integer from 1 to 6 can be prepared by a Willgerodt-Kindler reaction as illustrated by Diagram 2 below.

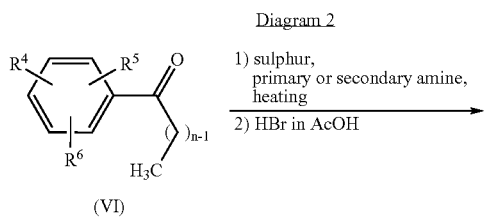

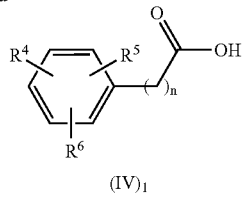

The arylketones of general formula (VI) in which $R^4$, $R^5$ and $R^6$ have the same meaning as that indicated for general formula (IV)$_1$ are treated with sulphur in the presence of an excess of primary or secondary amine (for example morpholine) while heating. After cooling down to ambient temperature and concentration to dryness, a solution of hydrobromic acid in acetic acid is added and the desired acid is obtained.

Preparation of the α-halogenoketones of General Formula (V)

The α-halogenoketones of general formula (V), when they are not commercially available, can be prepared from the corresponding ketones by halogenation methods known to a person skilled in the art. For example, in the case of an α-bromoketone, a reaction with a bromination agent can be used, such as CuBr$_2$ (*J. Org. Chem.* (1964), 29, 3459), bromine (*J. Het. Chem.* (1988), 25, 337), N-bromosuccinimide (*J. Amer. Chem. Soc.* (1980), 102, 2838) in the presence of acetic acid in a solvent such as ethyl acetate or dichloromethane, HBr or Br$_2$ in ether, ethanol or acetic acid (*Biorg. Med. Chem. Lett.* (1996), 6(3), 253-258; *J. Med. Chem.* (1988), 31(10), 1910-1918; *J. Am. Chem. Soc.* (1999), 121, 24) or also a bromination resin such as PVPHP (Poly(VinylPyridinium Hydrobromide Perbromide) resin in a solvent such as methanol, dichloromethane or toluene (*J. Macromol. Sci. Chem.* (1977), A11, (3) 507-514).

Unless otherwise defined, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented in order to illustrate the procedures above and should in no event be considered as a limit to the scope of the invention.

EXAMPLES

Example 1

4-(1,1'-biphenyl-4-yl)-2-(4-isobutylbenzyl)-1H-imidazole 1.1) (4-isobutylphenyl)acetic acid A mixture containing para-isobutylacetophenone (7 g; 40 mmol), 10 ml of morpholine and sulphur (2.45 g; 78 mmol) is taken to reflux for 18 hours. The reaction medium is then concentrated to dryness and 50 ml of a 33% solution of hydrobromic acid in acetic acid is added. The resultant mixture is heated to reflux for 3 hours then the temperature is left to return to 23° C. The reaction medium, to which small portions of toluene are added, is again concentrated to dryness. The residue is taken up in acetone and the salts filtered on frit. Animal black is added and the suspension heated to reflux for two hours, followed by filtration on celite, and the filtrate is concentrated to dryness before distillation under vacuum (P# 0.7 torr; T # 125-130° C.). A yellow-coloured solid is obtained at ambient temperature (yield of 33%). Melting point: 78-80° C.

1.2) 4-(1,1'-biphenyl-4-yl)-2-(4-isobutylbenzyl)-1H-imidazole

A mixture containing intermediate 1.1 prepared previously (1.2 g; 6.76 mmol) with cesium carbonate (1.1 g; 3.38 mmol) in 30 ml of methanol is stirred at ambient temperature for one hour. The solvent is evaporated off then the residue taken up in 30 ml of dimethylformamide. Then 2-bromo-4'-phenylacetophenone (1.85 g; 6.76 mmol) is added and the mixture left under stirring for 18 hours. The reaction medium is concentrated to dryness and the residue is taken up in 80 ml of xylene. After filtration on frit, ammonium acetate (10.4 g; 135 mmol) is added to the filtrate. The mixture obtained is heated to reflux for 2 hours, eliminating the water with a Dean Stark device.

Once the reaction mixture has returned to ambient temperature, it is poured into iced water. The ammonium acetate is neutralized with a saturated solution of $NaHCO_3$ before the phases are left to settle and extracted using ethyl acetate. The organic phase is then, with a saturated solution of sodium chloride, dried over magnesium sulphate and concentrated to dryness. After purification on a silica column (eluent: ethyl-heptane acetate: 2-8 to 6-4), a yellow-coloured powder is obtained (yield of 52%). Melting point: 160-161° C. MH+=367.3.

Example 2

2-hexyl-4-(4-isobutylphenyl)-1H-imidazole

2.1) 2-bromo-1-(4-isobutylphenyl)ethanone

Bromine (1.25 ml; 25 mmol) is added dropwise to a solution of 4'-isobutylacetophenone (3.52 g; 20 mmol) in 60 ml of ethanol cooled down to approximately 5° C. After stirring the reaction mixture for 30 minutes at this temperature, stirring is continued for one hour at ambient temperature. The reaction medium, to which small portions of toluene are added, is concentrated to dryness. After purification on a silica column (eluent: ethyl-heptane acetate: 5-95), a colourless oil is obtained with a yield of 57%.

NMR $^1$H (400 MHz): 0.85 (d, 6H); 1.84-1.92 (s, 1H); 2.53 (d, 2H); 4.89 (s, 2H); 7.33 (d, 2H); 7.93 (d, 2H).

2.2) 2-hexyl-4-(4-isobutylphenyl)-1H-imidazole

This compound is obtained according to an operating method analogous to that described for Stage 1.2 of Example 1. A white-coloured powder is obtained with a yield of 38%. Melting point: 89-90° C. MH+=285.2.

The compounds of Examples 3 to 18 are prepared from commercial products according to operating methods analogous to those of Examples 1 and 2, optionally completed by the general operating methods described in the part "Preparation of the compounds of the invention" (in particular with respect to the bromination in position α of the ketones).

Example 3

4-phenyl-2-(3-phenylpropyl)-1H-imidazole

White powder. Melting point: 106-108° C.

Example 4

2-(1-pentylhexyl)-4-phenyl-1H-imidazole

White powder. Melting point: 111.2° C.

Example 5

4-(4-fluorophenyl)-2-(1-pentylhexyl)-1H-imidazole

White powder. Melting point: 134.6° C.

Example 6

2-(cyclohexylmethyl)-4-(4-fluorophenyl)1H-imidazole

Light yellow foam. Melting point: 68-70° C.

Example 7

4-(1,1'-biphenyl-4-yl)-2-(1-pentylhexyl)-1H-imidazole

Light cream powder. Melting point: 173.6° C.

Example 8

4-(4-tert-butylphenyl)-2-(1-propylbutyl)-1H-imidazole

White powder. Melting point: 200-202° C.

Example 9

4-(4-fluorophenyl)-2-(1-propylbutyl)-1H-imidazole

Light cream powder. Melting point: 217.5° C.

Example 10

4-(4'-bromo-1,1'-biphenyl-4-yl)-2-(1-propylbutyl)-1H-imidazole

Light cream powder. Melting point: 182.8° C.

Example 11

4-(1,1'-biphenyl-4-yl)-2-(2-cyclohexylethyl)-1H-imidazole

Light cream powder. Melting point: 104.9° C.

Example 12

4-(1,1'-biphenyl-4-yl)-2-hexyl-1H-imidazole

Light cream powder. Melting point: 104.8° C.

Example 13

4-(1,1'-biphenyl-4-yl)-2-[1-(4-isobutylphenyl)ethyl]-1H-imidazole

Light yellow powder. Melting point: 172.7° C.

Example 14

4-(4-fluorophenyl)-2-[1-(4-isobutylphenyl)ethyl]-1H-imidazole

Light cream powder. Melting point: 116° C.

Example 15

4-(1,1'-biphenyl-4-yl)-2-(1-phenylethyl)-1H-imidazole

Light yellow powder. Melting point: 165-166° C.

Example 16

4-(1,1'-biphenyl-4-yl)-2-(1-propylbutyl)-1H-imidazole

Light yellow powder. Melting point: 197-198° C.

Example 17

4-(1,1'-biphenyl-4-yl)-2-(cyclohexylmethyl)-1H-imidazole

Light cream powder. Melting point: 104-105° C.

Example 18

4-(1,1'-biphenyl-4-yl)-2-(3-cyclohexylpropyl)-1H-imidazole

Light cream powder. Melting point: 118-119° C.

Pharmacological Study of the Products of the Invention

Binding Test on the Sodium Channels of Rat Cerebral Cortices

The test consists in measuring the interaction of the compounds vis-à-vis the binding of tritiated batrachotoxin on the voltage-dependent sodium channels according to the protocol described by Brown (*J. Neurosci.* (1986), 6, 2064-2070).

Preparation of Homogenates of Cerebral Cortices of the Rat

The cerebral cortices of Sprague-Dawley rats weighing 230-250 g (Charles River, France) are removed, weighed and homogenized using a Potter grinder provided with a teflon piston (10 strokes) in 10 volumes of isolation buffer the composition of which is as follows (sucrose 0.32 M, $K_2HPO_4$ 5 mM, pH 7.4). The homogenate is subjected to a first centrifugation at 1000 g for 10 minutes. The supernatant is removed and centrifuged at 20000 g for 15 minutes. The pellet is taken up in the isolation buffer and centrifuged at 20000 g for 15 minutes. The pellet obtained is resuspended in incubation buffer (HEPES 50 mM, KCl 5.4 mM, $MgSO_4$ 0.8 mM, glucose 5.5 mM, choline chloride 130 mM pH 7.4) then aliquoted and stored at −80° C. until the day of assay. The final protein concentration is comprised between 4 and 8 mg/ml. The assay of proteins is carried out using a kit marketed by BioRad (France).

Measurement of the Binding of Tritiated Batrachotoxin

The binding reaction is carried out by incubating for 1 hour 30 minutes at 25° C. 100 µl of homogenate of rat cortex containing 75 µg of proteins with 100 µl of [$^3$H] batrachotoxin-A 20-alpha benzoate (37.5 Ci/mmol, NEN) at 5 nM (final concentration), 200 µl of tetrodotoxin at 1 µM (final concentration) and scorpion venom at 40 µg/ml (final concentration) and 100 µl of incubation buffer alone or in the presence of the products to be tested at different concentrations. The non-specific binding is determined in the presence of 300 µM of veratridine and the value of this non-specific binding is subtracted from all the other values. The samples are then filtered using a Brandel (Gaithersburg, Md., USA) using Unifilter GF/C plates pre-incubated with 0.1% of polyethylene imine (20 µl/well) and rinsed twice with 2 ml of filtration buffer (HEPES 5 mM, $CaCl_2$ 1.8 mM, $MgSO_4$ 0.8 mM, choline chloride 130 mM, pH 7.4). After having added 20 µl of Microscint 0®, the radioactivity is counted using a liquid scintillation counter (Topcount, Packard). The measurement is carried out in duplicate. The results are expressed as a % of the specific binding of tritiated batrachotoxin relative to the control.

Results

The compounds of Examples 1 to 8 and 10 to 18 described above all have an $IC_{50}$ lower than or equal to 1 µM.

The invention claimed is:

1. A method of treating depression, bipolar disorder, and irritable bowel syndrome in warm blooded animals comprising administering to warm-blooded animals in need thereof an amount of a compound of the formula

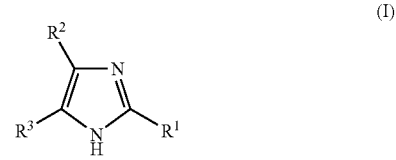

(I)

wherein $R^1$ is alkyl of 3 to 16 carbon atoms or a cycloalkylalkyl, the cycloalkyl of which contains 3 to 7 carbon atoms and the alkyl of which is 1 to 6 carbon atoms, or $R^1$ is aralkyl optionally substituted 1 to 3 times on the aryl with at least one member selected from the group consisting of halogen, alkyl and alkoxy of 1 to 6 carbon atoms;

$R^2$ is phenyl optionally substituted 1 to 3 times by at least one member selected from the group consisting of halogen, alkyl and alkoxy of 1 to 6 carbon atoms, or $R^2$ is biphenyl optionally substituted 1 to 4 times by at least one member of the group consisting of halogen, and alkyl and alkoxy of 1 to 6 carbon atoms;

$R^3$ is hydrogen or alkyl of 1 to 6 carbon atoms; and its pharmaceutically acceptable salts.

2. The method of claim 1 wherein the compound is selected from the group consisting of:

4-(1,1'-biphenyl-4-yl)-2-(4-isobutylbenzyl)-1H-imidazole;

2-hexyl-4-(4-isobutylphenyl)-1H-imidazole;

4-phenyl-2-(3-phenylpropyl)-1H-imidazole;

2-(1-pentylhexyl)-4-phenyl-1H-imidazole;

4-(4-fluorophenyl)-2-(1-pentylhexyl)-1H-imidazole;

2-(cyclohexylmethyl)-4-(4-fluorophenyl)-1H-imidazole;

4-(1,1'-biphenyl-4-yl)-2-(1-pentylhexyl)-1H-imidazole;

4-(4-tert-butylphenyl)-2-(1-propylbutyl)-1H-imidazole;

4-(4-fluorophenyl)-2-(1-propylbutyl)-1H-imidazole;
4-(4'-bromo-1,1'-biphenyl-4-yl)-2-(1-propylbutyl)-1H-imidazole;
4-(1,1'-biphenyl-4-yl)-2-(2-cyclohexylethyl)-1H-imidazole;
4-(1,1'-biphenyl-4-yl)-2-hexyl-1H-imidazole;
4-(1,1'-biphenyl-4-yl)-2-[1-(4-isobutylphenyl)ethyl]-1H-imidazole;
4-(4-fluorophenyl)-2-[1-(4-isobutylphenyl)ethyl]-1H-imidazole;
4-(1,1'-biphenyl-4-yl)-2-(1-phenylethyl)-1H-imidazole;
4-(1,1'-biphenyl-4-yl)-2-(1-propylbutyl)-1H-imidazole;
4-(1,1'-biphenyl-4-yl)-2-(cyclohexylmethyl)-1H-imidazole; and
4-(1,1'-biphenyl-4-yl)-2-(3-cyclohexylpropyl)-1H-imidazole;
and a pharmaceutically acceptable salt thereof.

3. The method of claim 1, wherein the compound is selected from the group consisting of:

4-(1,1'-biphenyl-4-yl)-2-(4-isobutylbenzyl)-1H-imidazole;
2-hexyl-4-(4-isobutylphenyl)-1H-imidazole;
2-(1-pentylhexyl)-4-phenyl-1H-imidazole;
4-(4-fluorophenyl)-2-(1-pentylhexyl)-1H-imidazole;
4-(1,1'-biphenyl-4-yl)-2-(1-pentylhexyl)-1H-imidazole;
4-(4-tert-butylphenyl)-2-(1-propylbutyl)-1H-imidazole;
4-(1,1'-biphenyl-4-yl)-2-(2-cyclohexylethyl)-1H-imidazole;
4-(1,1'-biphenyl-4-yl)-2-hexyl-1H-imidazole;
4-(1,1'-biphenyl-4-yl)-2-[1-(4-isobutylphenyl)ethyl]-1H-imidazole;
4-(1,1'-biphenyl-4-yl)-2-(1-propylbutyl)-1H-imidazole;
4-(1,1'-biphenyl-4-yl)-2-(cyclohexylmethyl)-1H-imidazole; and
4-(1,1'-biphenyl-4-yl)-2-(3-cyclohexylpropyl)-1H-imidazole;
and a pharmaceutically acceptable salt thereof.

* * * * *